United States Patent [19]

Hooper, Jr. et al.

[11] Patent Number: 4,688,558

[45] Date of Patent: Aug. 25, 1987

[54] ORTHOPEDIC APPLIANCE

[76] Inventors: Clarence R. Hooper, Jr., 819 Nottingham St., Orlando, Fla. 32803; Frederick E. Reed, 30 Bee St., Charleston, S.C. 29403

[21] Appl. No.: 862,962

[22] Filed: May 14, 1986

[51] Int. Cl.4 .............................. A61F 5/02
[52] U.S. Cl. ............................. 128/78; 2/44
[58] Field of Search .............. 128/78, 75, 69; 2/44

[56] References Cited

U.S. PATENT DOCUMENTS

| 894,066 | 7/1908 | Scarpa | 128/78 |
|---|---|---|---|
| 2,687,129 | 8/1954 | Talkish | 128/78 |
| 4,120,297 | 10/1978 | Rabinschong et al. | 128/78 |
| 4,202,327 | 5/1980 | Glancy | 128/78 |

FOREIGN PATENT DOCUMENTS

| 99783 | 2/1984 | European Pat. Off. | 128/78 |
|---|---|---|---|
| 583,590 | 9/1933 | Fed. Rep. of Germany | 128/78 |

Primary Examiner—Edgar S. Burr
Assistant Examiner—Moshe I. Cohen
Attorney, Agent, or Firm—William M. Hobby, III

[57] ABSTRACT

An orthopedic appliance apparatus for treatment of scoliosis has first and second polymer lateral shells, each formed with a curvature so that when connected together they will enclose the central portion of the body of a patient and apply an arcuate bending force to the spine opposite the lateral curvature of the spine. The shells are connected, one side with rivets and the other side with velcro straps which allows the tightening of the brace to fit the patient. Padding is positioned in predetermined positions with the greatest application of force as made against the body. One shell has a plurality of slots formed therein along one edge to allow expansion of the curvature of the shell.

9 Claims, 7 Drawing Figures

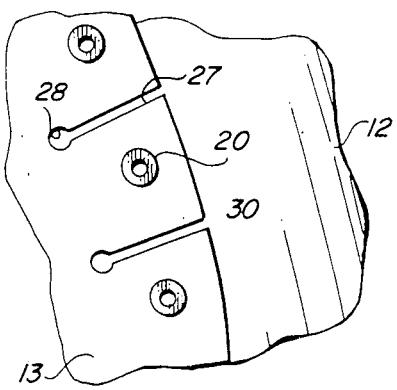
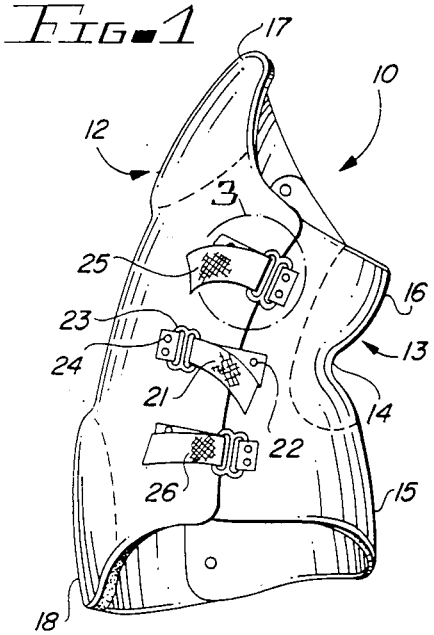
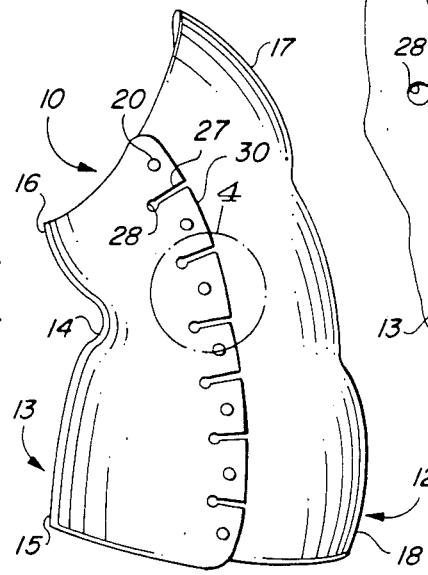
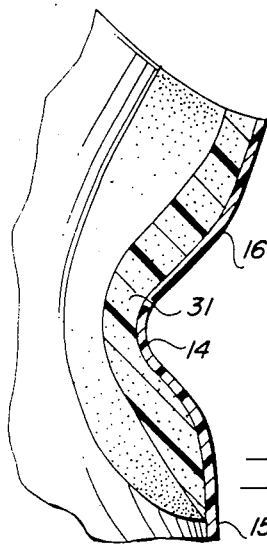
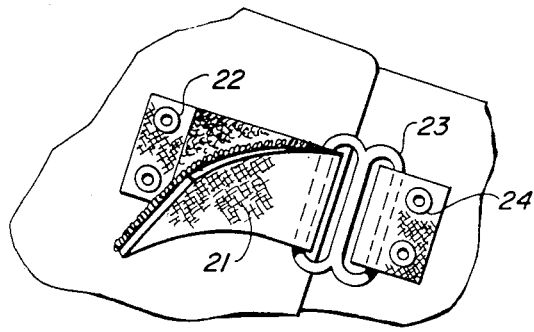
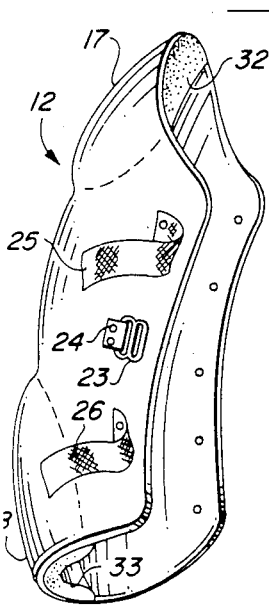
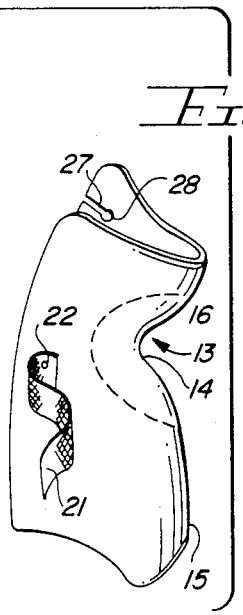
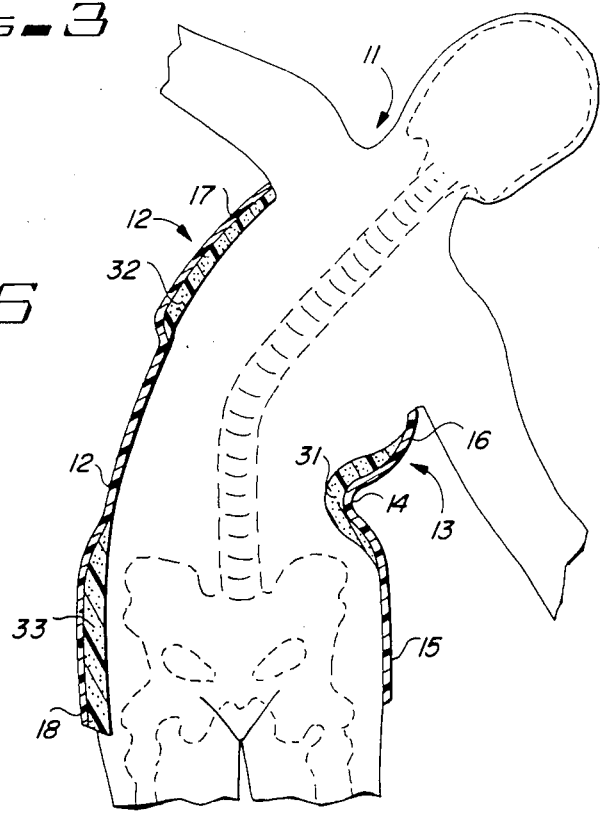

ORTHOPEDIC APPLIANCE

BACKGROUND OF THE INVENTION

The present invention relates to an orthopedic appliance and especially to an orthopedic brace for treating lateral curvature of the spine or scoliosis.

Scoliosis is the abnormal lateral curvature of the spine and maybe postural, a congenital deformity or the result of a neurological disease such as poliomyelitis. Scoliosis tends to run in families and is four times more common in girls than in boys.

A wide variety of orthopedic appliance have been utilized in the past for the treatment of various conditions including orthopedic braces for treating scoliosis. One such system utilizes a girdle or corset fitted to the wearers body and positioned around the pelvis and chest and appropriate attachments for the neck. Another prior structure utilizes a prefabricated girdle to which the super structure may be attached. One prior appliance is shown in U.S. Pat. No. 3,945,376 which unit utilizes various bars and straps joined by a rigid pelvic band positioned about the hips of the wearer and flexible iliac crest members on each side at the crest for top of the pelvic structure. In U.S. Pat. No. 2,687,129 a scoliosis brace is shown for treating lateral curvature of the spine and has a hip pad and chest pad joined together and joins with straps around the patients body and over his shoulder and allows for the adjustable tension means for engaging the body tangentially to point of greatest convexity of the spine. In U.S. Pat. No. 4,285,336 a scoliosis orthotic system has an anterior panel and a pair of posterior panels connected by pelvic bands and iliac crest members. In U.S. Pat. No. 3,878,841 shows an adjustable supportive and dynamic orthotic device for raising and supporting the shoulder of a surgical patient, while U.S. Pat. No. 1,935,859 shows an orthopedic appliance for the treatment of scoliosis having a plurality of adjustable pads innerconnected to the body of the patient.

The present invention differs from the prior art in that it is an orthopedic appliance for treating scoliosis only while the patient is asleep or in a lying position and forms a full body brace of two shells innerconnected to allow for adjustment of the curve on the patient and also provides for specific padding along the center of the inner curve and along the end portions of the outer curve shell or at the points where pressure applied by the brace to the patient. The present invention differs from all prior art previously described in that the bending and thus correcting force is applied directly to the spine and not indirectly through lateral and tangential forces to various parts of the body. An orthopedic appliance with a rigid body type requires straps specifically allowing for the adjustment of the pair of shells as well as slots to allow for curvature expansion of one of the shells. It allows the patient to wear the brace while asleep and then not have to wear the brace during daylight hours where it would generally impractical to wear an arcuate rigid body brace. The bend in the brace is so severe that the patient cannot stand while wearing the brace.

SUMMARY OF THE INVENTION

The present invention relates to orthopedic appliances and especially to an orthopedic brace for recumbant treatment of scoliosis including the use of a rigid body brace formed of a first polymer lateral shell and a second polymer lateral shell with the first polymer shell having a curvature in one direction therein and shaped to cover the patient's central body portion, while the second polymer shell forms a curvature in the opposite direction of the first shell and formed to mate with the first polymer shell to form an orthopedic appliance around the patient's bodice and extending from the hips to the arm pits. One curved edge of the first shell is attached to the curved edge of the second shell while the opposite curved edge of the first shell is held to the opposite edge of the second shell with a plurality of straps, such as hook and loop straps attached to one shell and looping through rings on the other shell. The first shell has a plurality of transverse extending slots along the attached edge to allow additional movement in the rigid polymer shell, which shells may be riveted therebetween. Foam padding is applied to the center of the inner curvature shell member while foam padding is applied to the portions away from the center of the second lateral shell of the outer curvature formed therein to thereby provide its own padding at the points of greatest pressure within the orthopedic appliance, thus, adding further to the bending of the curved spine. The orthopedic appliance applies a force opposite the lateral curvature of the spine of a scoliosis patient by forcing the patent to bend in an opposite direction to the patients spinal curvature.

BRIEF DESCRIPTION OF THE DRAWINGS

Other objects, features and advantages of the present invention will be apparent from the written description and the drawings in which:

FIG. 1 is a front elevation of a scoliosis appliance in accordance with the present invention;

FIG. 2 is a rear elevation of the appliance of FIG. 1;

FIG. 3 is a cutaway taken on the circle 3 of FIG. 1;

FIG. 4 is a cutaway taken on the circle 4 of FIG. 2;

FIG. 5 is a partial sectional view of the padding on the inner orthopedic brace shell;

FIG. 6 is an exploded perspective of the orthopedic appliance of FIGS. 1 and 2; and FIG. 7 is a sectional view of the orthopedic appliance of FIGS. 1 through 6 placed on a patient showing the relative position of the spine.

DESCRIPTION OF THE PREFERRED EMBODIMENT

Referring to the drawings, an orthopedic appliance 10 is illustrated for treating a patient 11 having scoliosis or lateral curvature of the spine. The apparatus is specifically directed towards a rigid body brace for treating scoliosis in the patent in a lying position, such as when the patient is asleep. It is not worn during daylight hours when the patient is actively pursueing daily activities. Orthopedic brace 10 has a first polymer lateral shell 12, and a second lateral shell 13. Shell 13 has an inner curvature shaped to fit across one side of the patients body as shown in FIG. 7 with a sharp arcuate section 14 located between the iliac portion 15 and the upper chest portion 16, while the shell 12 has a more general arcuate shape but extending higher on the rib cage at the top portion 17 and lower over the iliac 18. The shells 12 and 13 are held together along lateral edges by a plurality of rivets 20 connecting the two shells together on one side while the lateral edge on the opposite side are held together with hook and loop fasteners 21. Hook and loop fasteners have an elongated strip of hook and loop 21 on the center strap attached with the rivets 22 to shell 13 and extending around a metal loop 23 attached with rivets 24 to the shell 12, while an upper hook and loop strap 25 and a lower hook and loop strap 26 are attached in the same manner except that the hook and loop is attached to the shell 12 while the loops are attached to the shell 13. On the opposite side of the curved appliance is a plurality of slots 27 having a small aperture 28 at the end thereof positioned along the edge 30 between the rivets 20. The slots allow for slight expansion in the curvature of the shell 13 during the tightening of the straps 21, 25 and 26, without cracking or breaking the polymer material in the shell 13. The shells may be made of a polypropylene molded to the particular shape shown, which is specifically fitted to the body to allow the body to be held in a position to force the spine in a position as shown in FIG. 7 against the normal curvature of the patients spine of a scoliosis patient. Thus the interior curvature 14 of the interior shell 13 is shaped to force the body to be held in a curved position against the iliac braced area 15 and the rib cage brace area 16 and has a foam padding 31 therein with the thickest against the center of the curvature 14 and tapering in thickness towards either end thereof. The polymer shell 12 has raised portions 17 which fit against the upper rib cage and a raised portion 18 for fitting against the persons iliac area for the placement of foam padding 32 under the raised portion 17 and foam padding 33 under the raised portion 18 so that the pressure areas on the exterior lateral shell 12 applies the pressure against the rib cage and against the ilium through the foam padded material, while the interior curvature of the shell 13 is padded at the pressure points 14 in the center of the shell. The shell can be rapidly attached and easily removed by the unstrapping of the hook and loop straps 21, 25 and 26 and opening up the shells from this side. The rivets 20 have enough give, especially against the slots 27, to allow the patient to slide in and out of the hard shell orthopedic appliance. The straps being located on the front of the appliance allow the patient to quickly loop the straps and pull the straps tight to apply the necessary bending for the corrective action to the spine of the patient. Thus the shells are joined posteriorly along their edges with rivets and interiorly with hook and loop straps.

It should be clear at this point that a rigid two piece polymer scoliosis brace has been provided for use by patients when in a lying position such as when sleeping and which can be rapidly adjusted by the patient to apply greater pressure in a rigid brace and to allow for additional pressures within the rigid brace against the patients body. The curvature of the brace bends the spine opposite to the bend of a scoliosis patient's spine rather than attempting to merely hold the spine straight. The bend in the brace will not allow the patient to stand or move about. However, it should also be clear that the present invention is not to be considered limited to the forms as shown which are to be considered illustrative rather then restrictive.

I claim:

1. An orthopedic appliance for a recumbant treatment of scoliosis comprising in combination:

a first polymer lateral shell formed with a curvature in one direction therein and shaped to fit over a portion of the patients bodice;
   a second polymer lateral shell formed with a curvature in the opposite direction complimentary to the curvature of the first polymer lateral shell and formed to mate with the first polymer lateral shell to form an orthopedic appliance, said second polymer lateral shell having one curved edge attached to an oppositely curved edge of the first polymer lateral shell; means for adjusting the curvature of said first shell including a plurality of slots extending transversely from the curved edge of the first shell attached to the curved edge of the second shell to provide additional curvature in said orthopedic appliance, each of said slots having a round aperture at one end thereof,
   a plurality of strap fasteners with portions connected to a second curved edge of said second polymer lateral shell and to a second curved edge of said first polymer lateral shell oppositely curved edge for adjustably fastening the first and second shell edges together; and whereby a solid scoliosis brace is adjustable for curvature with a plurality of straps on a pair of connected rigid shells.

2. An orthopedic appliance in accordance with claim 1 in which said first polymer lateral shell has padding positioned therein along the center of inner curved portion thereof.

3. An orthopedic appliance in accordance with claim 2 in which said second polymer has a padding placed therein against the shell portion placed adjacent the pelvis of a patient and the shell portion is expanded to receive the padded portion therein.

4. An orthopedic appliance in accordance with claim 3 in which a second polymer lateral shell portion has padding placed therein to fit adjacent the upper rib cage of the patient and the rigid shell has an expanded portion for receiving the padding therein.

5. An orthopedic appliance in accordance with claim 1 in which said first polymer lateral shell and said second lateral shell are each formed of polypropylene.

6. An orthopedic appliance in accordance with claim 5 in which said plurality of straps includes at least one hook and loop strap attached to the first polymer lateral shell for looping around a loop attached to the second polymer shell.

7. An orthopedic appliance in accordance with claim 6 in which said second polymer lateral shell has at least one hook and loop material strap attached thereto for attaching to a loop attached to the first polymer lateral shell.

8. An orthopedic appliance in accordance with claim 7 in which said first polymer lateral shell has a piece of hook and loop material strap attached in the center portion thereto while the second polymer lateral shell has a hook and loop strap attached to both sides of the center of the lateral shell so that tightening different straps will vary the pressure, bending force and curvature of the lateral shells.

9. An orthopedic appliance in accordance with claim 1 in which said first polymer lateral shell and said second polymer lateral shell are connected to each other along one edge thereof with rivets.

* * * * *